(12) United States Patent
Fernandez Puentes et al.

(10) Patent No.: US 6,656,948 B2
(45) Date of Patent: Dec. 2, 2003

(54) CYTOTOXIC COMPOUNDS: DERIVATIVES OF THE PYRIDO[2,3,4-KL]ACRIDINE RING SYSTEM

(75) Inventors: José Luis Fernandez Puentes, Leon (ES); Dolores Garcia Gravalos, Madrid (ES); Carmen Avendano Lopez, Madrid (ES); Maria del Mar Blanco Castro, Madrid (ES); Jose Carlos Menendez Ramos, Madrid (ES)

(73) Assignee: Universidad Complutense de Madrid, Madrid (ES)

( * ) Notice: Subject to any disclaimer, the term of this patent is extended or adjusted under 35 U.S.C. 154(b) by 0 days.

(21) Appl. No.: 09/962,013

(22) Filed: Sep. 24, 2001

(65) Prior Publication Data

US 2002/0128281 A1 Sep. 12, 2002

Related U.S. Application Data

(63) Continuation of application No. 09/429,204, filed on Oct. 28, 1999, now abandoned, which is a continuation of application No. PCT/GB98/01239, filed on Apr. 29, 1998.

(51) Int. Cl.[7] ..................... A61K 31/435; C07D 471/00
(52) U.S. Cl. ......................................... 514/280; 546/48
(58) Field of Search ............................. 546/48; 514/280

(56) References Cited

U.S. PATENT DOCUMENTS 5,182,287 A   1/1993 Gunawardana et al. ..... 514/260

OTHER PUBLICATIONS

CA 133:237987, Deflourne et al. 2000.*
CA 133:105194, Blanco et al. 2000.*
CA 129:216805, Kitahara et al. 1998.*
CA 127: 81657, Kitahara et al. 1997.*
CA 135: 34468, Delfourne et al. 2001.*

Gomez–Bengoa et al., "Synthesis of Isoascididemnin, a Regioisomer of the Marine Alkaloide Ascididemnin", *J. Org. Chem.* 1991, vol. 56, pp. 3497–3501.

Molinski, "Marine Pyridoacridine Alkaloids: Structure, Synthesis, and Biological Chemistry", *Chem. Rev.* 1993, vol. 93, pp. 1825–1838.

Schmitz et al., "Biologically active compounds from marine organisms", *Pure & Appl. Chem.,* 62, No. 7, pp. 1393–1396, 1990.

Kitahara et al., "Synthesis of Meridine, A Pentacyclic Aza–Aromatic Alkaloid", *Chem. Pharm Bull.,* vol. 42(6), pp. 1363–1364 (1994).

* cited by examiner

*Primary Examiner*—Jane Fan
(74) *Attorney, Agent, or Firm*—Fish & Richardson P.C.

(57) ABSTRACT

Compounds of the following formula:

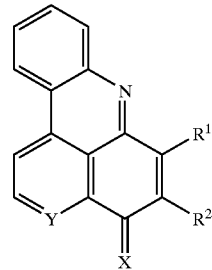

wherein all variables are as defined in the specification. The compounds have cytotoxic properties and can therefore be used in the treatment of malignant tumors.

11 Claims, No Drawings

CYTOTOXIC COMPOUNDS: DERIVATIVES OF THE PYRIDO[2,3,4-KL]ACRIDINE RING SYSTEM

CROSS REFERENCE TO RELATED APPLICATIONS

This application is a continuation of U.S. patent application Ser. No. 09/429,204, filed Oct. 28, 1999, now abandoned, which is a continuation of PCT Application No. GB98/01239, filed Apr. 29, 1998, which claims priority to Great Britain Application No. 9708751.4, filed Apr. 29, 1997.

BACKGROUND OF THE INVENTION

The present invention relates to a series of new polycyclic aromatic alkaloids having a pyrido[2,3,4-k,l]acridine skeleton which have cytotoxic properties and which can therefore be used in the treatment of malignant tumours. The invention also provides methods and compositions using these new compounds as well as processes for their preparation.

The polycyclic aromatic alkaloids based on the pyrido[2,3,4-k,l]acridine skeleton are a growing class of ascidian metabolites that often exhibit a variety of interesting biological properties, including antitumour activity.[1] This class of compounds comprises three main structural types, depending of the position of the fusion between the parent structure and additional rings present in the natural product. For example, the cystoditines[2] have the base skeleton mentioned above, while amphimedine,[3] meridine[4] and cystodamine[5] bear an additional pyridine ring attached to the h bond; ascididemin,[6] its derivatives,[7] the kuanoniamines[8] and shermilamine A[9] show this additional ring at the i face, and eilatine at both.[10] Our target compounds can be regarded as regioisomers both of meridine and amphimedine, but they have not been so far isolated from natural sources.

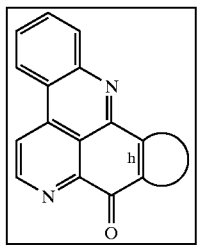

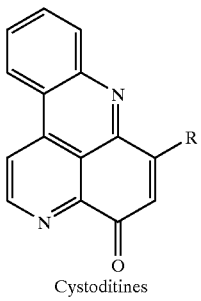
Cystoditines

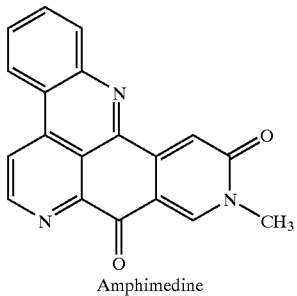
Amphimedine

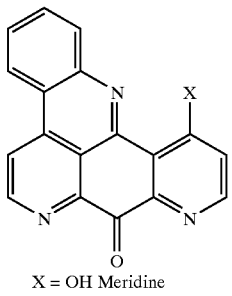
X = OH Meridine
X = NH₂ Cystodamine

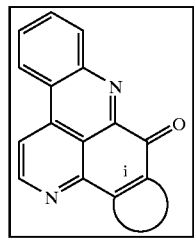

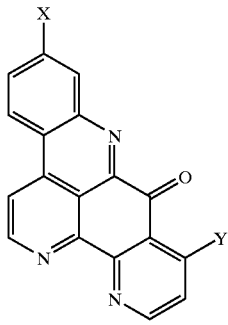

| X | Y | Compound |
|---|---|---|
| H | H | Ascididemine (leptoclinidinone) |
| Br | H | 2-Bromoleptoclinidinone |
| H | OH | 11-Hydroxyascididemine (neocallisctine) |

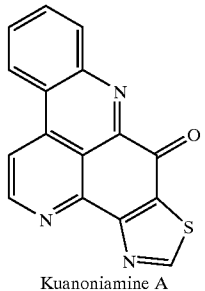
Kuanoniamine A

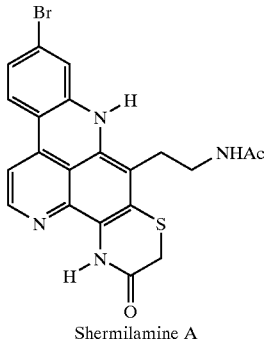
Shermilamine A

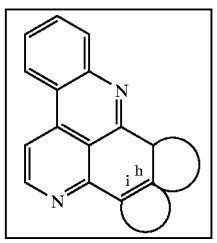

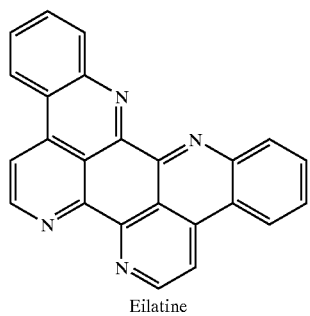
Eilatine

Most of these prior art compounds exhibit very interesting cytotoxic properties towards a range of tumor cell lines. Although their mechanism of action is not clearly established, three general observations emerge from published biological data:[11] a) they are intercalating agents; b) they disrupt DNA and RNA synthesis, with little effect on protein synthesis; c) they inhibit topoisomerase II, which is the mechanism normally accepted for their antitumour activity.

Biological studies on pyridoacridines are severely limited due to their very low availability from natural sources, and therefore the study of their mechanism of action and the establishment of reliable structure-activity relationships requires the development of efficient synthetic routes.

DEFINITION OF THE INVENTION

We have now discovered a new family of polycyclic aromatic alkaloids having a pyrido[2,3,4-k,l]acridine skeleton which show excellent antitumour activity.

Thus, in a first aspect of the present invention there is provided compounds having the general formula (I):

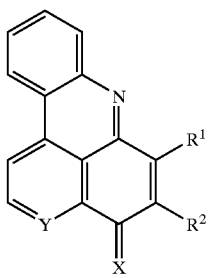

(I)

wherein:
X is selected from the group consisting of O, and $NR^3$, where $R^3$ represents a lower alkyl group;
Y is selected from the group consisting of CH and N;
$R^1$ and $R^2$ are independently selected from the group consisting of $NH_2$, $NHR^4$ and $NR^5{}_2$, where $R^4$ and $R^5$ each represent a lower alkyl group, or $R^1$ and $R^2$ together represent a cycle selected from (a), (b) and (c):

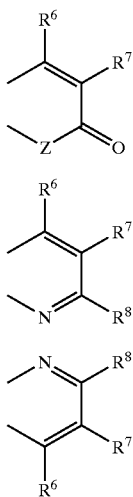

wherein $R^6$, $R^7$ and $R^8$ are independently selected from the group consisting of hydrogen atoms, lower alkyl groups, hydroxy groups and lower alkoxy groups; and Z is selected from the group consisting of O and NH; and pharmaceutically acceptable salts thereof.

In the definitions of the groups in formula (I), the lower alkyl groups and the lower alkyl moiety of the lower alkoxy groups are straight-chain or branched alkyl groups having 1 to 6 carbon atoms such as methyl, ethyl, propyl, isopropyl, butyl, isobutyl, sec-butyl, tert-butyl, pentyl, neopentyl and hexyl groups.

For those compounds of the present invention wherein $R^1$ and $R^2$ together represent a cycle of formula (a), $R^6$ and $R^7$ are preferably independently selected from the group consisting of hydrogen atoms, alkyl groups having from 1 to 4 carbon atoms, hydroxy groups and alkoxy groups having from 1 to 4 carbon atoms; more preferably, $R^6$ and $R^7$ are independently selected from the group consisting of hydrogen atoms, methyl groups and ethyl groups; and, most preferably, $R^6$ represents a methyl group and $R^7$ represents a hydrogen atom. Furthermore, where $R^1$ and $R^2$ together represent a cycle of formula (a), it is preferable that Z represents a group of formula NH.

For those compounds of the present invention wherein $R^1$ and $R^2$ together represent a cycle of formula (b) or (c), $R^6$, $R^7$ and $R^8$ are preferably selected from the group consisting of hydrogen atoms, alkyl groups having from 1 to 4 carbon atoms, hydroxy groups and alkoxy groups having from 1 to 4 carbon atoms; more preferably, $R^6$, $R^7$ and $R^8$ are independently selected from the group consisting of hydrogen atoms, methyl groups, ethyl groups and hydroxy groups; and, most preferably, $R^6$ represents a hydroxy group and $R^7$ and $R^8$ each represent a hydrogen atom.

In a preferred embodiment, the present invention relates to novel synthetic compounds of general structure (II) or (III):

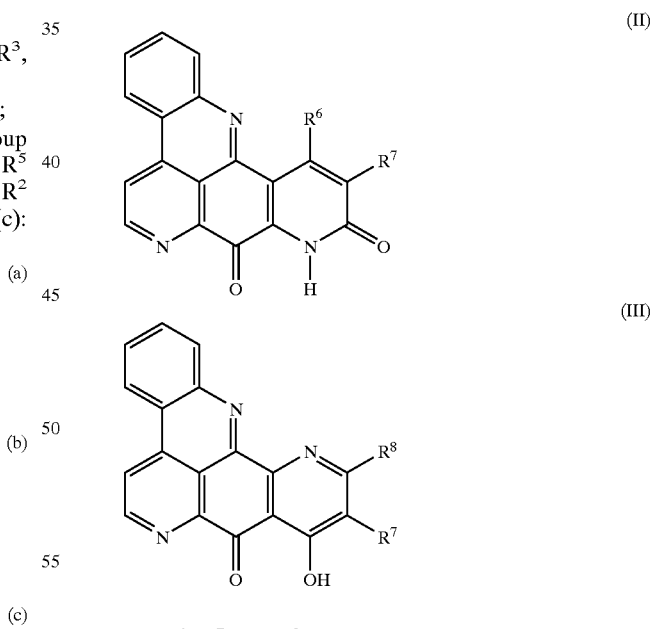

wherein $R^6$, $R^7$ and $R^8$ are as defined above.

Of the compounds of general formula (II), we particularly prefer the compound wherein $R^6$ represents a methyl group and $R^7$ represents a hydrogen atom (Compound No. IB-96213).

Of the compounds of general formula (III), we particularly prefer the compound wherein $R^7$ and $R^8$ both represent a hydrogen atom (Compound No. IB-98205).

The present invention also provides a method for treating a mammal affected by a malignant tumor sensitive to a compound having the general formula (I), which comprises administering to the affected individual a therapeutically effective amount of the compound having the general formula (I) or a pharmaceutical composition thereof.

The present invention further provides pharmaceutical compositions, particularly useful in the treatment of malignant tumors, which contain as the active ingredient a compound having the general formula (I), as well as a process for the preparation of said compositions.

A further aspect of the present invention provides a method for preparing the compounds of general formula (I) and, in particular, Compounds Nos. IB-96213 and IB-98205.

Our strategy for the synthesis of the target compounds involves an hetero Diels-Alder reaction between an o-nitrogenated 4-aryl-1-dimethylamino-1,4-azadiene and a suitable heterocyclic quinone, followed by nucleophilic cyclization onto one of the quinone carbonyls (Scheme 1).

Scheme 1

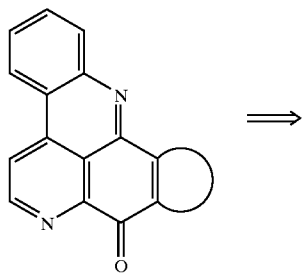

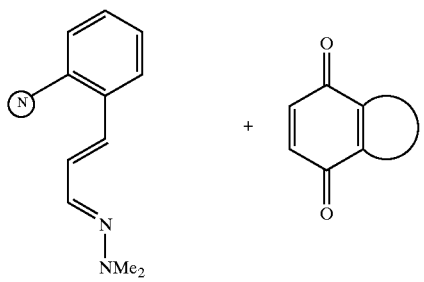

Ⓝ = nitrogen function

Among the several 4-aryl-1-azadienes assayed, the best results were obtained for the o-nitro and the o-(trifluoroacetamido) derivatives. The first of them (compound 1a) was prepared from commercially available o-nitrocinnamaldehyde using a known procedure[12]. For the second azadiene (compound 1b), two alternative syntheses were devised (Scheme 2). The first of them involved trifluoroacetylation of the corresponding o-amino derivative 2, prepared by reduction of compound 1a[12]. In the second synthesis, o-aminobenzaldehyde (3) was N-trifluoroacetylated and the amide was used as a Wadsworth-Emmons coupling partner with compound 5.[13]

Scheme 2

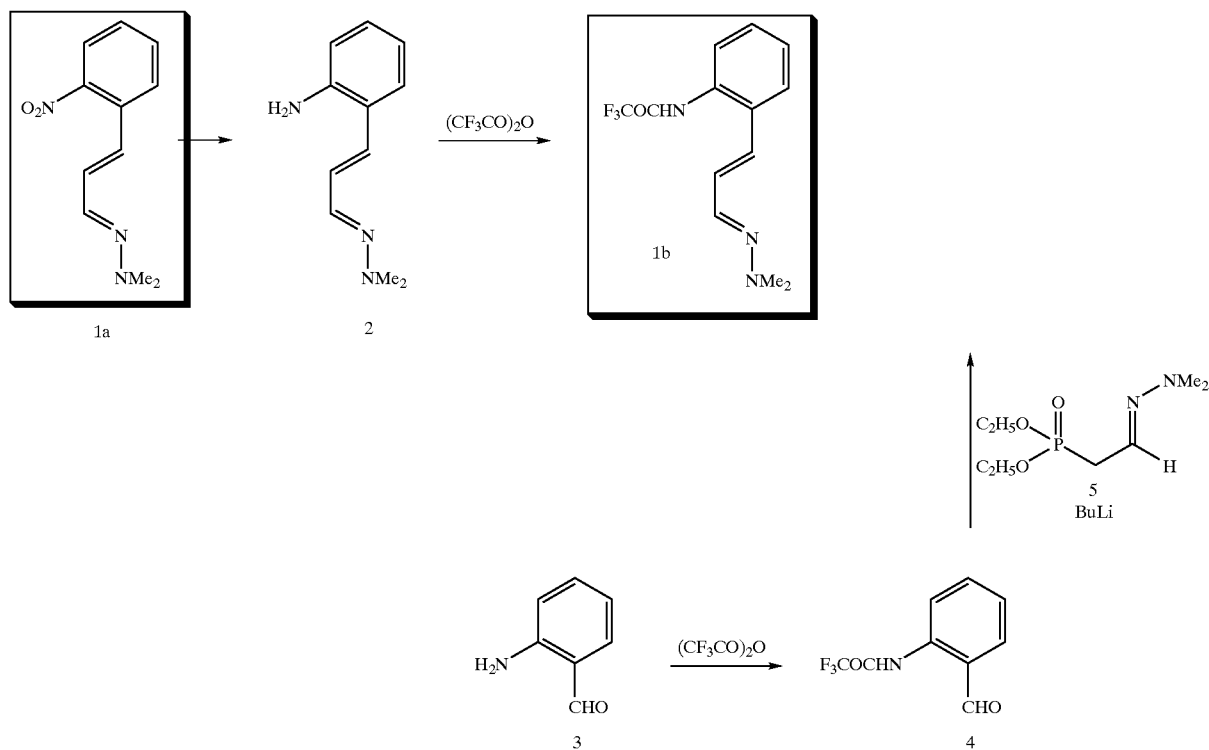

The reaction between 1b and quinones 6[14] to produce compounds of formula (II) was carried out in refluxing chloroform, and led to a mixture of the Diels-Alder adducts 7 and the secondary products 8. Compounds 7 were aromatized to 9 by refluxing in the presence of Pd-C in methanol solution, and 9 was finally transformed into the desired pentacyclic derivatives 10 [general structure (II)] by hydrolytic cyclization (Scheme 3).

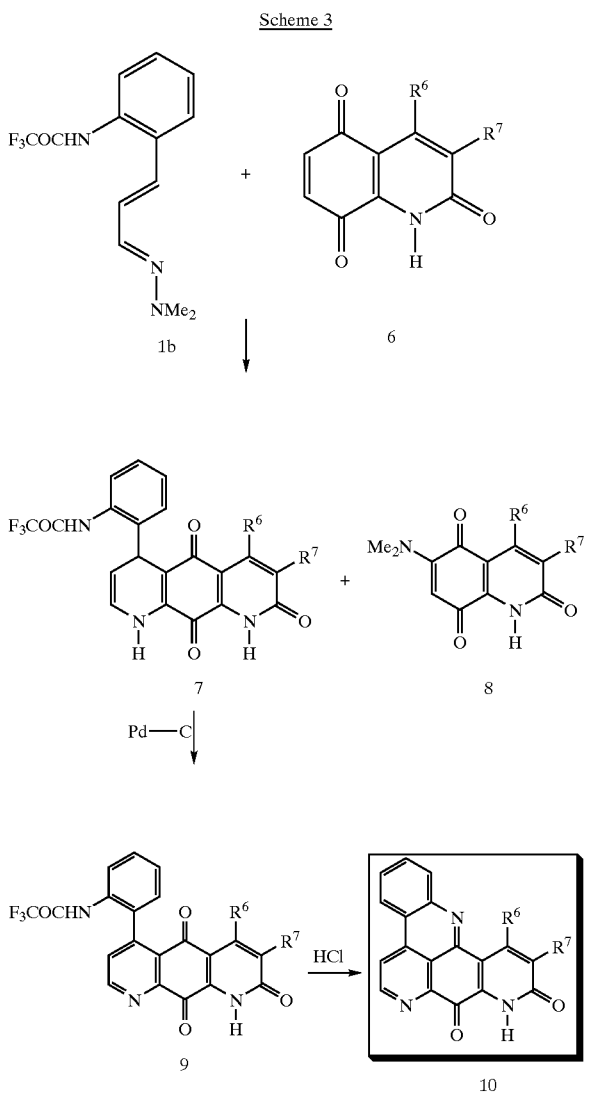

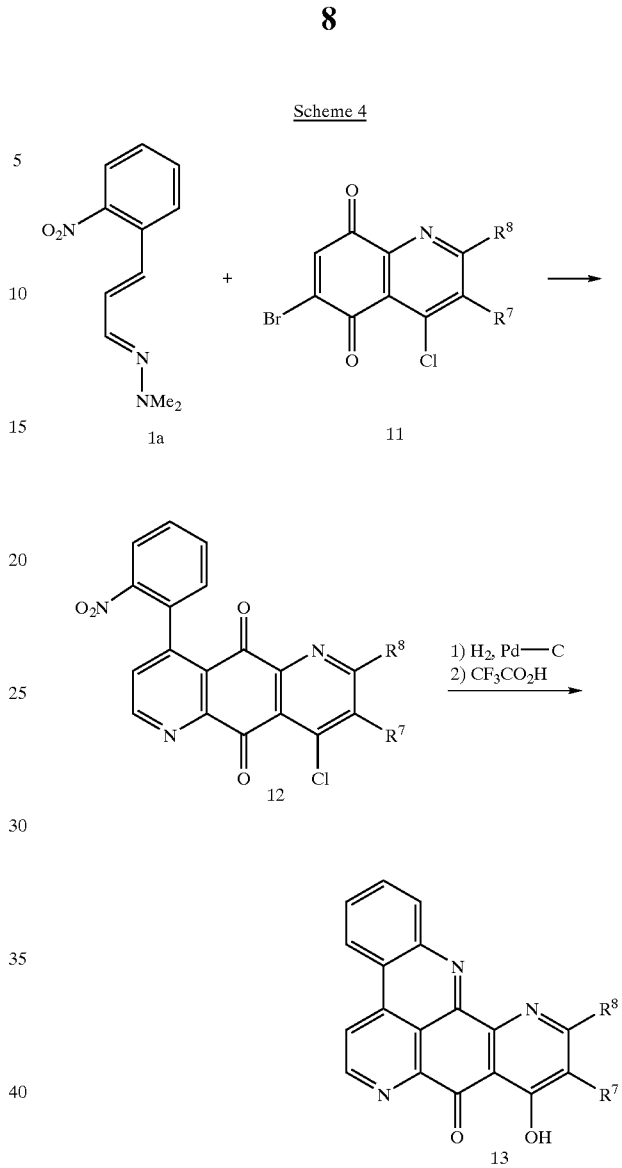

The use of 6-bromo-4-chloroquinolinequinones 11 as dienophiles led to reversal of the regioselectivity of the hetero Diels-Alder reaction. Thus, treatment of azadiene 1a with 11 under ultrasound irradiation afforded compound 12. Hydrogenation of 12 in the presence of Pd-C followed by workup with trifluoroacetic acid gave pyridoacridines 13 [general structure (III)] (Scheme 4).

As examples, the detailed procedure for the synthesis of 12-methyl-9H-benzo[b]pyrido[4,3,2-d,e](1,7)phenantr IB-96213 (general structure 10, where $R^6=CH_3$, $R^7=H$) and 9-hydroxybenzo[b]pyrido[4,3,2-d,e](1,10)phenantrolin-8-one IB-98205 (general structure 13, where $R^7=R^8=H$) are given in the experimental section.

The compounds of the present invention are cytotoxic, compounds such as IB-96213 and IB-98205 exhibiting antitumor activity, especially against cell lines derived from human solid tumors, such as human lung carcinoma, human colon carcinoma and human melanoma, and, the like. They are also active against other tumor cell lines, like leukemia and lymphoma. Compounds of formula (I), such as IB-96213 and IB-98205, have in vitro antitumor selectivity for solid tumors.

Examples of pharmaceutical compositions include any solid (tablets, pills, capsules, granules, etc.) or liquid (solutions, suspensions or emulsions) dosage form, with suitable formulation of oral, topical or parenteral administration, and they may contain the pure compound or in combination with any carrier or other pharmacologically active compounds. These compositions may need to be sterile when administered parenterally.

The correct dosage of a pharmaceutical composition comprising compounds with formula (I), will vary according to the pharmaceutical formulation, the mode of application, and the particular situs, host and tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

Experimental

The invention is further illustrated by the following Examples, which demonstrate the preparation of various of the compounds of the present invention. The reagents used were of commercial origin (Aldrich, Fluka) and were employed without further purification. Solvents (SDS, Scharlau) were purified and dried by standard procedures. Reactions were monitored by thin-layer chromatography, using Scharlau and Macherey-Nagel plates with fluorescent indicator. Separations by flash liquid chromatography were performed using silica gel SDS 60 ACC (230–400 mesh).

Melting points are uncorrected, and were determined in open capillary tubes, using a Büchi immersion apparatus or a Hoffler hot stage microscope. Combustion elemental analyses were obtained by the Servicio de Microanalisis Elemental, Universidad Complutense, using a Perkin Elmer 2400 CHN analyzer. Spectroscopic data were obtained with the following instruments: IR, Perkin Elmer 577 and Perki Elmer Paragon 1000 FT-IR; NMR, Varian VXR-300 (300 MHz for $^1$H and 75 MHz for $^{13}$C) and Bruker AC-250 (250 MHz for $^1$H and 63 MHz for $^{13}$C).

EXAMPLE 1

12-Methyl-9H-benzo[b]pyrido[4,3,2-d,e](1,7) phenantroline-8,10-dione (IB-96213; a compound of fo Step 1(a) 4-(o-Trifluoroacetamidophenyl)-1-dimethylamino-1-azadiene (Formula 1b)

Method A

Trifluoroacetic anhydride (1.39 g, 6.63 mmol) was added dropwise to a stirred solution of 4-(o-aminophenyl)-1-dimethylamino-1-azadiene (2)[12] (837 mg, 4.42 mmol) in dry ethyl ether (10 ml). The solution was stirred at room temperature for 15 min and evaporated under reduced pressure at room temperature. The residue was purified by chromatography on silica gel, eluting with dichloromethane to give the title compound 1b; yield, 1.023 g (88%).

Data for 1b:

Mp, 110° C.
Analysis. Calcd. for $C_{13}H_{14}F_3N_3$: C, 54.73: H, 4.91; N, 14.73
Found: C, 54.10; H, 4.19; N, 14.11
IR (KBr): 3250 (NH), 1655 (CO).
$^1$H-NMR (250 MHz, CDCl$_3$) d: 8.01 (1H, s, NHCOCF$_3$); 7.69 (1H, m, $C_3$-H); 7.52 (1H, m, $C_6$-H); 7.25 (2H, m, $C_{4,5}$-H); 7.08 (1H, d, J = 8.9 Hz, $C_2$-H); 6.88 (1H, dd, J = 15.6 and 8.9 Hz, $C_3$-H); 6.50 (1H, d, J = 15.6 Hz, $C_4$-H); 2.88 (6H, s, CH$_3$).
$^{13}$C-NMR (63 MHz, CDCl$_3$) d: 155.14 (d, J = 37.1 Hz, CO); 133.43 ($C_2$); 1313.84 ($C_3$); 128.00 ($C_4$); 127.54 ($C_5$); 126.30 ($C_6$); 124.61 ($C_3$); 123.25 ($C_4$); 115.66 (q, J = 288.0 Hz, CF$_3$); 42.39 (NMe$_2$).

Method B.

a) o-(trifluoroacetamido)benzaldehyde (4). To a suspension of o-nitrobenzaldehyde (3 g, 19.86 mmol) in 35% aqueous hydrochloric acid (35 ml) was added 21 g (93.1 mmol) of tin (II) chloride in small portions. The suspension was stirred at room temperature for 72 h, neutralized with 6N aqueous sodium hydroxide and extracted with chloroform (4×50 ml). The combined chloroform layers were dried over sodium sulphate and evaporated, yielding 1.87 g (78%) of o-aminobenzaldehyde 3. A part of this residue (1.26 g, 10.4 mmol) was dissolved in dry ethyl ether (5 ml). This solution was cooled to 0° C. and treated dropwise with trifluoroacetic anhydride (2 ml, 14.15 mmol), while magnetically stirred. The solution was stirred for 2 h at room temperature. The solvent was evaporated and the residue was chromatographed on silica gel, eluting with a 7:3 petroleum ether-dichloromethane mixture. Yield, 1.65 g (77%) of compound 4.

Data for 4:

Mp, 71–72° C.
Analysis. Calcd. for $C_9H_6F_3NO_2$: C, 49.78: H, 2.79; N, 6.45
Found: C, 49.70; H, 2.59; N, 6.11
$^1$H-NMR (250 MHz, CDCl$_3$) d: 10.21 (1H, s, NHCOCF$_3$); 9.99 (1H, m, $C_3$-H); 8.69 (1H, d, J = 8.4 Hz, $C_3$-H); 7.81 (1H, dd, J = 7.6 and 5.6 Hz, $C_6$-H); 7.72 (1H, td, J = 7.9 and 1.6 Hz, $C_5$-H); 7.41 (1H, t, J = 7.4 Hz, $C_4$-H).
$^{13}$C-NMR (63 MHz, CDCl$_3$) d: 195.62 (CO); 155.70 (d, J = 38.1 Hz, CO); 138.05 ($C_1$); 136.32 ($C_4$); 136.04 ($C_5$); 125.22 ($C_6$); 122.47 ($C_2$); 120.32 ($C_3$); 115.44 (q, J = 289.2 Hz, CF$_3$).

b) Wadsworth-Emmons reaction between compounds 4 and 5. To a stirred solution of hydrazone 5[13] (see Scheme 2) in dry tetrahydrofuran placed in a −78° C. bath was added a solution of butyl lithium in hexanes (0.1 ml, 1.1 mmol). The coloured solution was stirred for 40 min at the same temperature and a solution of the aldehyde 4 (217 mg, 1 mmol) in dry tetrahydrofuran (1 ml) was then added. The reacting mixture was stirred at 0° C. for 4 h, quenched by addition of a saturated aqueous solution of ammonium chloride (10 ml) and extracted with chloroform (4×15 ml). The combined extracts were dried over sodium sulphate and evaporated and the residue was chromatographed on silica gel, eluting with 1:1 ethyl ether-petroleum ether. Yield, 103 mg (36%) of the title compound 1b.

Step 1(b) 5-(o-Trifluoroacetamido)-4methyl-5,8-dihydro-1, 8-diazaanthracene-2,9,10-trione (a compound of formula 7 in which $R^6=CH_3$ and $R^7=H$)

A solution of quinone 6 (see Scheme 3; $R^6=CH_3$, $R^7=H$) [14a] and azadiene 1b produced according to Step 1(a) above (32 mg, 0.17 mmol) in chloroform (50 ml) was refluxed in a bath at 60° C. for 22 h, while a stream of argon was forced through the solution. The reaction mixture was evaporated to dryness and the residue was purified by chromatography on silica gel, eluting with a gradient from 3:2 dichloromethane-ethyl acetate to neat ethyl acetate, yielding 25 mg (34%) of the title 5,8-dihydro derivative 7 ($R^6=CH_3$, $R^7=H$), 20 mg (28%) of the aromatic compound 9 (see Scheme 3; $R^6=CH_3$ and 11 mg (28%) of compound 8 (see Scheme 3; $R^6=CH_3$, $R^7=H$).[14a]

Data for 7:

Mp 192° C. (AcOEt)
Analysis. Calcd. for $C_{21}H_{14}F_3N_3O_4$: C, 58.77: H, 3.36; N, 9.78
Found: C, 58.49; H, 3.62; N, 9.57
IR (KBr): 3364 (NH); 1726, 1661 (CO) cm$^{-1}$.

Data for 7:

$^1$H-NMR (250 MHz, CDCl$_3$) d: 11.93 (1H, br, s, NH); 11.28 (1H, s, NHCOCF$_3$); 9.30 (1H, br, s, NH) 7.37–7.32 (4H, m, C$_{2'-6'}$-H); 6.50 (1H, s, C$_3$-H); 6.35 (1H, m, C$_7$-H); 4.96 (1H, m, C$_6$-H); 4.78 (1H, d, J = 4.7 Hz, C$_5$-H); 2.37 (3 H, s, CH$_3$).

Data for 9:

Mp 285° C.
Analysis. Calcd. for C$_{21}$H$_{12}$F$_3$N$_3$O$_4$:   C, 59.04: H, 2.80; N, 9.83
Found:                           C, 59.22; H, 2.94; N, 9.59
IR (KBr): 3178 (NH); 1733, 1664 (CO) cm$^{-1}$.
$^1$H-NMR (250 MHz, CDCl$_3$) d: 10.00 (1H, br, s, NH); 9.02 (1H, d, J = 4.8 Hz, C$_7$-H); 8.21 (1H, s, NHCOCF$_3$); 7.70 (1H, d, J = 7.6 Hz, C$_6$-H); 7.58 (1H, td, J = 7.6 and 1.5 Hz, C$_4$-H); 7.53 (1H, d, J = 4.8 Hz, C$_6$-H); 7.42 (1H, td, J = 7.6 and 1.5 Hz, C$_5$-H); 7.16 (1H, dd, J = 7.6 and 1.5 Hz, C$_3$-H); 6.46 (1H, d, J = 1.1 Hz, C$_3$-H); 2.46 (3 H, d, J = 1.1 Hz, CH$_3$).

Step 1(c) Oxidation of 7 to 9

To a suspension of compound 7 (R$^6$=CH$_3$, R$^7$=H), produced according to Step 1(b) above, [200 mg, 0.46 mmol in methanol (50 ml)] was added solid 10% palladium on charcoal (100 mg, 9 mmol). The suspension was refluxed for 48 h, while vigorously stirred, and filtered through celite. The solvent was evaporated, yielding 136 mg (69%) of the title compound 9 (R$^6$=CH$_3$, R$^7$=H).

Step 1(d) 12-Methyl-9H-benzo[b]pyrido[4,3,2-d,e](1,7)phenantroline8,10-dione (IB-96213; compound of formula 10, R$^6$=CH$_3$ and R$^7$=H)

To a solution of compound 9 (R$^6$=CH$_3$, R$^7$=H) produced according to Step 1(d) above, in methanol (15 ml) was added 2 N aqueous hydrochloric acid (2 ml). The solution was refluxed for 4 h, neutralized with 8% aqueous sodium bicarbonate and extracted with chloroform. Evaporation of the organic layer gave 57 mg (78%) of the title compound 10 (R$^6$=CH$_3$, R$^7$=H).

Data for 10:

Mp > 300° C. (CHCl$_3$)
Analysis. Calcd. for C$_{19}$H$_{11}$N$_3$O$_2$:   C, 72.86: H, 3.51; N, 13.41
Found:                           C, 72.87; H, 2.82; N, 13.57
IR (KBr): 3418 (NH); 1648 (CO and C = N) cm$^{-1}$.
$^1$H-NMR (250 MHz, F$_3$C—CO$_2$D) d: 9.24 (1H, br. s, C$_6$-H); 9.03 (1H, br. s, C$_5$-H); 8.57 (1H, d, J = 7.7 Hz, C$_4$-H); 8.22 (1H, d, J = 7.7 Hz, C$_1$-H); 7.96 (1H, t, J = 7.3 Hz, C$_2$-H); 7.79 (1H, t, J = 7.3 Hz, C$_3$-H); 6.45 (s, 1H, C$_{11}$-H); 2.45 (s, 3H, C$_{12}$-CH$_3$) ppm.

EXAMPLE 2

9-Hydroxybenzo[b]prido[4,3,2-d,e](1,10)phenantrolin-8-one (IB-98205: a compound of formula 13 in which R$^7$=R$^8$=H)

Step 2(a) 4-Chloro-8-(o-nitrophenyl)-1,5-diazaanthraquinone (a compound of formula 12 in which R$^7$=R$^8$=H)

A solution of quinone 11 (see Scheme 4; R$^7$=R$^8$=H)$^{15}$ (185 mg, 0.68 mmol) and o-nitrocynamma dimethylhydrazone 1a$^{12}$ (438mg, 2 mmol) in chloroform (1 mL) was irradiated with ultrasound at 50° C. for 125 h. The solvent was evaporated and the residue was chromatographed on silica gel, eluting with ethyl acetate to give the title compound 11; yield, 52 mg (20%).

Data for 12:

Mp, 146° C.
Analysis. Calcd. for C$_{18}$H$_8$ClN$_3$O$_4$:   C, 59.13: H, 2.18; N, 11.48
Found:                              C, 59.89; H, 1.99; N, 11.17
IR (KBr)u: 1689 (C=O) cm$^{-1}$.
$^1$H-NMR (250 MHz, CDCl$_3$) δ: 9.15 (d, 1H, J = 4.8 Hz, H-6); 8.81 (d, 1H, J = 5.1 Hz, H-2); 8.34 (dd, 1H, J = 7.6 and 1.3 Hz, H-3'); 7.77 (ddd, 1H, J = 7.6, 7.6 and 1.3 Hz, H-5'); 7.72 (d, 1H, J = 5.1 Hz, H-3); 7.67 (ddd, 1H, J = 7.6, 7.6 and 1.3 Hz, H-4'); 7.49 (d, 1H, J = 4.8 Hz, H-7); 7.28 (dd, 1H, J = 7.6 and 1.3 Hz, H-6') ppm.
$^{13}$C-NMR (63 MHz, CDCl$_3$) δ: 180.66, 179.54, 155.03, 154.05, 150.36, 149.86, 149.34, 146.91, 145.98, 134.15, 134.03, 131.06, 129.84, 129.59, 128.44, 127.09, 126.61, 124.93, 121.46 ppm Step 2(b) 9-Hydroxybenzo[b]pyrido[4,3,2-d,e](1,10)phenantrolin-8-one (13, R$^7$=R$^8$=H To a solution of compound 12 (100 mg, 0.27 mmol), produced according to Step 2(a) above, and triethylamine (37 mg) in methanol (25 mL) was added 10% palladium on charcoal (22 mg). The suspension was hydrogenated at 1 atm for 1 h and filtered through celite. The celite layer was washed with a 2:1 mixture of trifluoroacetic acid and chloroform (25 mL). These washings were evaporated and chromatographed on silica gel, eluting with 9:1 ethyl acetate methanol, affording 45 mg of a mixture of two reduction intermediates, whose structure was not determined. To a solution of 35 mg of this mixture in methanol (20 mL) was added 10% palladium on charcoal (8 mg), and the suspension was hydrogenated at 1 atm for 1 h and filtered through celite. The solution was evaporated and the residue was chromatographed on silica gel, yielding 6 mg (10%) of the title compound 13.

$^1$H-NMR (250 MHz, CF$_3$COOH) δ: 9.30(d); 9.15(d); 8.73(d); 8.36(m); 8.10(m); 7.99(m); 7.48(d); 7.34(d) ppm.

The present inventors have prepared by the preceding synthetic pathway the following specific compounds, IB-96213 (general structure 10, were R$^6$=CH$_3$ and R$^7$=H) and IB-98205 (general structure 13, were R$^7$=R$^8$=H) which are specially preferred herein:

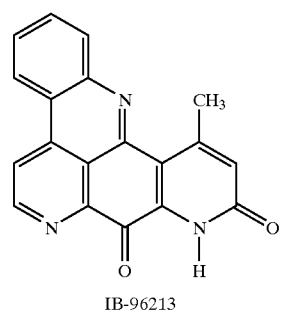

IB-96213

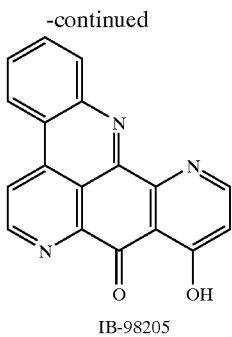

IB-98205

Biological Activity

The compounds of formula (I) of the present invention show good antitumor activity. In particular, IB-96213 and IB-98205 display good antitumor activity against several mammalian cancer cell lines. Its antitumor activity has been detected in vitro by culturing the tumor cells following the methodology described by Bergeron et al. [16], and by Schroeder et al [16]. Activity against different tumors as mouse lymphoma, human NSC lung carcinoma, human melanoma and human colon carcinoma has been observed.

Some tumors were more sensitive than others. As for example it was found that NSC lung carcinoma and melanoma cells were 100 times more sensitive than mouse lymphoma and 1000 times more sensitive than human colon carcinoma cells.

EXAMPLE

Biological activity: Cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); suplemented with 10% Fetal Calf Serum (FCS), $10^{-2}$ M sodium bicarbonate and 0,1 g/l penicillin-G+ streptomycin sulfate.

The tumor cell lines employed have been P-388 (ATCC CCL-46, suspension culture of a lymphoid neoplasm from DBA/2 mouse), A-549 (ATCC CCL-185, monolayer culture of a human lung carcinoma), HT-29 (ATCC HTB-38, monolayer culture of a human colon carcinoma) and MEL-28 (ATCC HTB-38, monolayer culture of a human melanoma).

P-388 cells were seeded into 16 mm wells at $1\times10^4$ cells per well in 1 ml aliquots of MEM 5FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humide atmosphere, an aproximate $IC_{50}$ was determined by comparing the growth in wells with drug to the growth in wells control.

A-549, HT-29 and MEL-28 were seeded into 16 mm wells at $2\times10^4$ cells per well in 1 ml aliquots of MEM 10FCS containing the indicated concentration of drug. A separate set of cultures without drug was seeded as control growth to ensure that cells remained in exponential phase of growth. All determinations were carried out in duplicate. After three days of incubation at 37° C., 10% $CO_2$ in a 98% humide atmosphere, the wells were stained with 0.1% Crystal Violet. An aproximate $IC_{50}$ was determined by comparing the growth in wells with drug to the growth in wells control.

In Table I are presented the cytotoxicity expressed as $IC_{50}$ in µg/ml and µM

TABLE I

| | $IC_{50}$ µg/ml(µM) | | | |
|---|---|---|---|---|
| COMPOUND | P-388 ATCC CCL-46 | A-549 ATCC- CCL-185 | HT-29 ATCC HTB-38 | MEL-28 ATCC HTB-38 |
| IB-96213 | 0.1(0.32) | 0.001(0.003) | 1(3.18) | 0.001(0.003) |
| IB-98205 | 1.25(4.18) | 0.012(0.04) | 0.12(0.40) | 0.05(0.17) |

REFERENCES

1. Reviews: a) T. F. Molinsky, Chem. Rev. 1993, 93, 1825. b) M. Alvarez, J. A. Joule, *Heterocycles*, 1992, 34, 2385. c) M. Alvarez, M. Salas, J. A. Joule, *Heterocycles*, 1991, 32, 759.
2. J. Kobayashi, J. Cheng, M. R. Walchii, H. Nakamura, Y. Hirata, T. Sasaki, Y. Ohizumi, *J. Am. Chem. Soc.,* 1988, 53, 1800.
3. F. J. Schmitz, S. K. Agarwal, S. P. Gunasekera, *J. Am. Chem. Soc.,* 1983, 105, 4835.
4. F. J. Schmitz, F. S. de Guzman, M. B. Hossain, D. van der Helm, *J. Org. Chem.,* 1991, 56, 804.
5. N. Bontemps, I. Bonnard, B. Banaigs, G. Combaut, C. Francisco, *Tetrahedron Lett.,* 1994, 35, 7023.
6. J. Kobayashi, J.-F. Cheng, H. Nakamura, Y. Ohizumi, Y. Hirata, T. Sasaki, T. Ohta, S. Nozoe, *Tetrahedron Lett.,* 1988, 29, 1177.
7. 2-Bromoleptoclinidone: S. J. Bloor, F. J. Schmitz, *Tetrahedron Lett.,* 1989, 30, 1069. Neocalliactine acetate: F. Bracher, *Liebigs Ann. Chem.,* 1992, 1205.
8. A. R. Carroll, P. J. Scheuer, *J. Org. Chem.,* 1990, 55, 4426.
9. N. M. Cooray, P. J. Scheuer, L Parkanyi, J. Clardy, *J. Org. Chem.,* 1988, 53, 4619.
10. A. Rudi, Y. Kashman, *J. Org. Chem.,* 1989, 54, 5331.
11. a) F. J. Schmitz, F. S. de Guzman, Y.-H. Choi, M. B. Hossain, S. K. Rizui, D. van der Helm, *Pure Appl. Chem.,* 1990, 62, 1393. b) L. A. McDonald, G. S. Edredge, L. R. Barrows, C. M. Ireland, *J. Med. Chem.,* 1994, 37, 3819. c) B. S. Lindsay, L. R. Barrows, B. R. Copp, *Bioorg. Med. Chem. Lett.,* 1995, 5, 739.
12. A. M. Echavarren, *J. Org. Chem.* 1990, 55, 4525.
13. R. E. Dolle, W. P. Armstrong, A. N. Shaw, R. Novelli, *Tetrahedron Lett.,* 1988, 29, 6349.
14. The quinones used as dienophiles (compounds 6) were prepared from 2,5-dimethoxyaniline using previously published procedures: a) C. Avendaño, E. de la Cuesta, C. Gesto, *Synthesis,* 1991, 727. b) M. M. Blanco, C. Avendaño, N. Cabezas, J. C. Menéndez, *Heterocycles,* 1993, 36, 1387. c) M. A. Alonso, M. M. Blanco, C. Avendaño, J. C. Menéndez, *Heterocycles,* 1993, 36, 2315. d) L. M. Diaz-Guerra, B. Ocaña, J. M. Pérez, C. Avendaño, M. Espada, J. C. Menéndez, M. T. Ramos, M. A. Ruiz, J. M. Pingarrón, D. Salvatierra, C. Jaime, *Bull. Soc. Chim. Belg.,* 1995, 104, 683. e) P. López-Alvarado, C. Avendaño, J. C. Menéndez, *Synthesis,* 1998, 186.
15. Gómez-Bengoa, E.; Echavarren, A.M., *J. Org. Chem.,* 1991, 56, 3497.
16. Raymond J. Bergeron, Paul F. Cavanaugh, Jr., Steven J. Kline, Robert G. Hughes, Jr., Gary T. Elliot and Carl W. Porter. Antineoplastic and antiherpetic activity of spermidine catecholamide iron chelators. *Biochem. Bioph. Res. Comm.* 1984, 121(3): 848–854.
17. Alan C. Schroeder, Robert G. Hughes, Jr. and Alexander Bloch. Effects of Acyclic Pyrimidine Nucleoside Analoges. *J. Med. Chem.* 1981, 24:1078–1083.

What is claimed is:

1. A compound of formula (I):

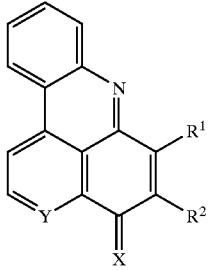

(I)

wherein:

X is O;

Y is N;

$R^1$ and $R^2$ together represent a cycle selected from (a) and (b):

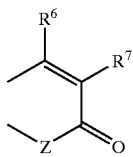

(a)

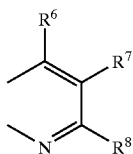

(b)

wherein $R^6$ and $R^7$ are independently selected from the group consisting of hydrogen atoms, lower alkyl groups, hydroxy groups and lower alkoxy groups; and $R^8$ is hydroxy;

and

Z is NH;

or a pharmaceutically acceptable salts thereof.

2. A compound according to claim 1, wherein $R^1$ and $R^2$ together represent a cycle of formula (a).

3. A compound according to claim 2, wherein $R^6$ and $R^7$ are independently selected from the group consisting of hydrogen atoms, alkyl groups having from 1 to 4 carbon atoms, hydroxy groups and alkoxy groups having from 1 to 4 carbon atoms.

4. A compound according to claim 3, wherein $R^6$ and $R^7$ are independently selected from the group consisting of hydrogen atoms, methyl groups and ethyl groups.

5. A compound according to claim 4, wherein $R^6$ represents a methyl group and $R^7$ represents a hydrogen atom.

6. A compound according to claim 1 having the following formula (II):

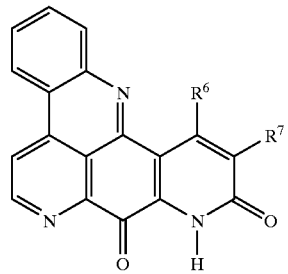

(II)

wherein $R^6$ and $R^7$ are as defined in claim 1.

7. A compound according to claim 6, wherein $R^6$ represents a methyl group and $R^7$ represents a hydrogen atom.

8. A pharmaceutical composition comprising a compound of formula (I) as defined in any one of claims 1, 2, 3, 4, 5, in admixture with a pharmaceutically acceptable carrier or diluent.

9. A pharmaceutical composition according to claim 8 having antitumor activity against human lung carcinoma.

10. A method for treating a mammal affected by a malignant lung tumor, comprising the administration to the affected individual of an effective amount of a compound of formula (I) according to any one of claims 1, 2, 3, 4, or 5.

11. A process for the production of compounds of formula (II), as defined in claim 6, comprising:

a) reaction of a compound of formula Ib:

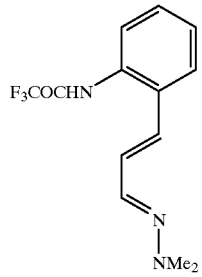

1b with a compound of formula 6:

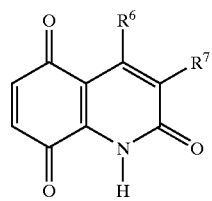

6 wherein $R^6$ and $R^7$ are independently selected from the group consisting of hydrogen atoms, lower alkyl groups, hydroxy groups and lower alkoxy groups, to give a compound of formula 7:

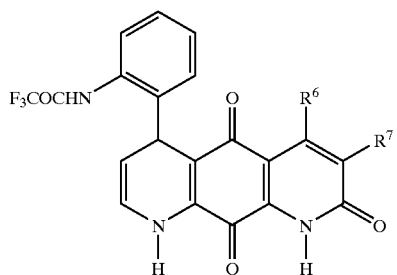

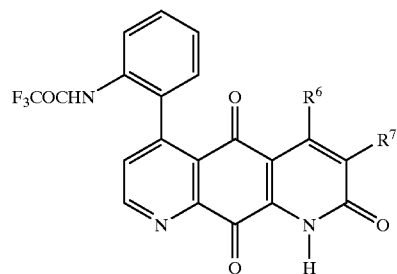

wherein $R^6$ and $R^7$ are independently selected from the group consisting of hydrogen atoms, lower alkyl groups, hydroxy groups and lower alkoxy groups;

(b) aromatization of the compound of formula 7 in the presence of a Pd-C catalyst, to give a compound of formula 9:

wherein $R^6$ and $R^7$ are independently selected from the group consisting of hydrogen atoms, lower alkyl groups, hydroxy groups and lower alkoxy groups; and (iii) hydrolytic cyclization of the compound of formula 9 to give the compound of formula (II).

* * * * *